US00PP16670P2

(12) United States Plant Patent
Boeder

(10) Patent No.: US PP16,670 P2
(45) Date of Patent: Jun. 20, 2006

(54) ***CHRYSANTHEMUM* PLANT NAMED 'ARTIST ORANGE'**

(50) Latin Name: *Chrysanthemum morifolium*
Varietal Denomination: Artist Orange

(75) Inventor: Mark Roland Boeder, The Hague (NL)

(73) Assignee: Chrysanthemum Breeders Association N.V. (NL)

( * ) Notice: Subject to any disclaimer, the term of this patent is extended or adjusted under 35 U.S.C. 154(b) by 75 days.

(21) Appl. No.: 11/020,351

(22) Filed: Dec. 27, 2004

(51) Int. Cl.
*A01H 5/00* (2006.01)

(52) U.S. Cl. ..... Plt./296

(58) Field of Classification Search ..... Plt./296
See application file for complete search history.

*Primary Examiner*—Anne Marie Grunberg
*Assistant Examiner*—Annette H Para
(74) *Attorney, Agent, or Firm*—Steptoe & Johnson LLP

(57) ABSTRACT

A *Chrysanthemum* plant named 'Artist Orange' characterized by its medium sized daisy-type blooms with yellow/red ray-florets and green disc florets.

3 Drawing Sheets

RELATED CULTIVARS

'Artist Orange' is related to 'Artist Yellow' (U.S. Plant Pat. No. 14,806), of which it is a color mutant.

BACKGROUND OF THE INVENTION

'Artist Orange' is a product of a breeding and selection program which had the objective of finding color mutants of 'Artist Yellow'. The new plant of the present invention comprises a new and distinct cultivar of *chrysanthemum* plant that is a natural occurring sport of a parent *chrysanthemum* named 'Artist Yellow'. A comparison with parent *chrysanthemum* 'Artist Yellow' is also made in this application. The new and distinct cultivar was discovered as a whole plant mutation by Mark Roland Boeder in a controlled environment (greenhouse) in Rijsenhout Holland in 2002. The first act of asexual reproduction of 'Artist Orange' was accomplished when vegetative cuttings were taken from the initial selection in 2002 and propagated in a controlled environment in Rijsenhout, Holland.

SUMMARY OF THE INVENTION

The present invention is a new and distinct variety of *chrysanthemum* bearing medium sized daisy blooms with orange/red ray-florets and green disc florets.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
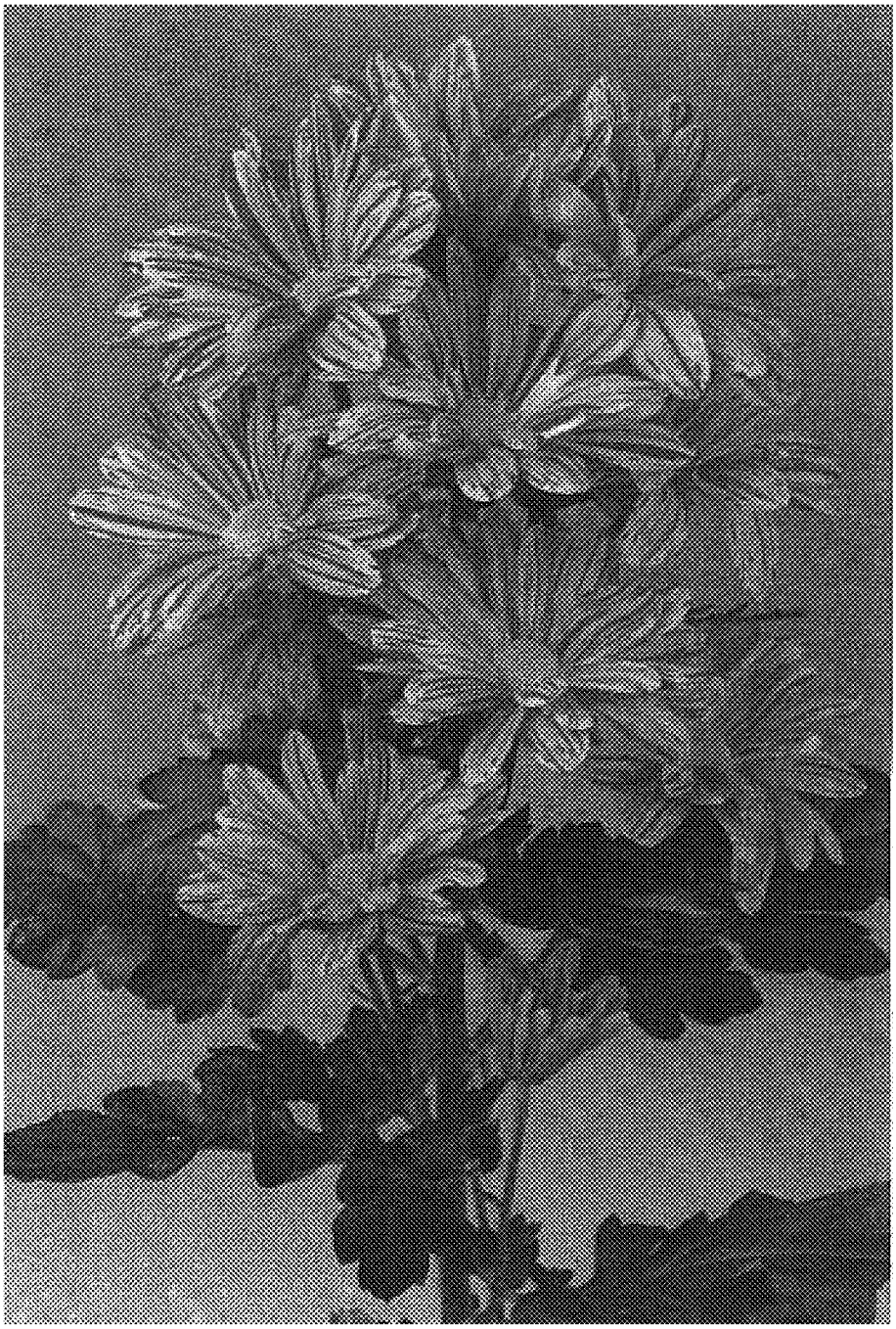
FIG. 1 shows a plant of the cultivar in full bloom.
Figure 2:
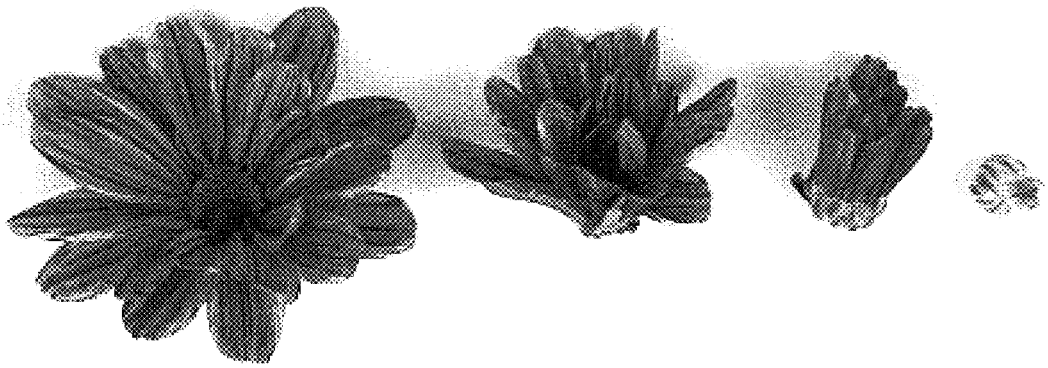
FIG. 2 shows the various stages of bloom of the new cultivar.
Figure 3:
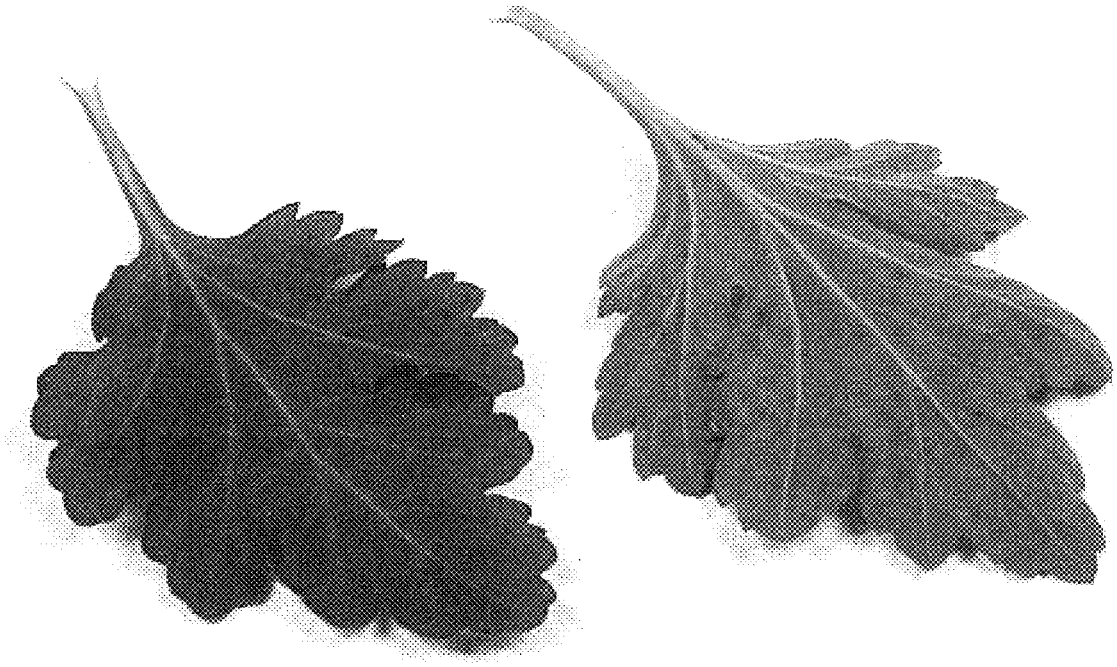
FIG. 3 shows the foliage of the new cultivar.

This new variety of *chrysanthemum* is of the botanical classification *Chrysanthemum morifolium* L. The observations and measurements were gathered from plants grown in April/May in a greenhouse in Rijsenhout Holland in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 54 days. After the long day period to flowering plant growth retardants were applied once in a dose of 2 gram/liter water. The plants were observed (directly) during the flowering of this crop. The plant is sensitive to infestation by Powdery Mildew. The plant is tolerant to low night temperatures. This new variety produces medium sized blooms with yellow/red ray-florets and green disc-florets blooming on the plant for 5 weeks. This new variety of *chrysanthemum* has been found to retain its distinctive characteristics throughout successive propagations however the phenotype may vary significantly with variations in environment such as light intensity and temperature. To show the phenotype as described 'Artist Orange' can be planted without assimilation lightning (high pressure sodium lamps) between week 1 and week 35 under greenhouse conditions in Holland. With assimilation light (minimum level 2500 lux) it can be planted year round under greenhouse conditions in Holland.

From the cultivars known to inventor the most similar existing cultivar in comparison to 'Artist Orange' is 'Artist Yellow' and 'Orange Reagan' (U.S. Plant Pat. No. 8,769). When 'Artist Orange', 'Artist Yellow', and 'Orange Reagan' are being compared the following differences and similarities are noticed: All three plants have daisy-type blooms. The difference of 'Artist Orange', 'Artist Yellow' and 'Orange Reagan' is the color of the ray-florets. In 'Orange Reagan' this color is orange, while it is in 'Artist Orange' a pattern of red streaks on an orange background, and in 'Artist Yellow' red streaks on a yellow background.

The following is a description of the plant and characteristics that distinguish 'Artist Orange' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

| Botanical Description of CULTIVAR 'Artist Orange' | |
|---|---|
| Bud | |
| Size | Medium, cross-section 1 cm height 1 cm |
| Outside color | Orange 29 B |
| Involucral bracts | 2 rows, length 7 mm, width 3 mm |
| Involucral bracts among disc-florets | Not present |
| Involucral bracts color | Green 141 B |
| Bloom | |
| Type | Daisy |
| Size | Medium |
| Fully expanded | 5–6 cm |
| Number of blooms per stem | Average of 14 |
| Performance on the plant | 5 weeks |
| Seeds (if crossed) | Produced in large quantities, oval shaped, Grey-brown 199 A, 2 mm in length |
| Fragrance | Typical *chrysanthemum,* slight |
| Peduncle length | Near the top 6 cm, near the middle 11 cm, near the bottom 21 cm |
| Peduncle color | Green 143C–D |
| Color | |
| Center of the flower (disc-florets) | Immature Yellow-green 154 C Mature Yellow-orange 15A |
| Color of the ray-florets | Upper surface Orange 29A with streaks of Red 45B Lower surface Greyed Orange 164C with streaks of Greyed-Orange 173B |
| Tonality from Distance | A spray mum with orange/red flowers and green disc |
| Color of the upper surface of the ray-florets after aging of the plant | Orange 29A with streaks of Red 45B |
| Ray florets | |
| Texture | Upper and under side smooth |
| Number | 25 |
| Cross section | Flat |
| Longitudinal axis of majority | Straight |
| Length of corolla tube | 0.4 cm |
| Ray-floret margin | Entire |
| Ray-floret length | 2.8–3 cm |
| Ray-floret width | 0.9 cm |
| Ratio length/width | Medium |
| Shape of tip | Rounded |
| Disc florets | |
| Disc diameter | 1 cm |
| Distribution of disc florets | Numerous, clearly visible at all stages of flowering. |
| Shape | Tubular |
| Receptacle shape | Domed Raised |
| Reproductive Organs | |
| Stamen (present in disc florets only) | Thin 3 mm in length |
| Stamen color | Yellow-green 144 B |
| Pollen | Present |
| Pollen color | Yellow-orange 14 A |
| Styles (present in both ray and disc florets) | Thin |
| Style color | Yellow-green 150 B |
| Style length | 0.4 cm |

TABLE 1-continued

| Botanical Description of CULTIVAR 'Artist Orange' | |
|---|---|
| Stigma color | Yellow-green 144 B |
| Stigma width | 0.2 cm |
| Ovaries | Enclosed in perianth |
| Plant | |
| Form | A spray mum meant for erect culture |
| Growth habit | Upright |
| Growth rate | Vigorous |
| Height | 90 cm |
| Width | 25 cm |
| Internode length | 2.5–3 cm |
| Spray formation | Cylindrical |
| Stem Color | Green 138A–B |
| Stem Strength | Strong |
| Stem Brittleness | Not brittle |
| Stem Anthocyanin coloration | Absent |
| Flowering Response (photo-periodic controlled crop, not natural season) | 54 days |
| Foliage | |
| Color immature stage | Upper side Green 143B–144B Lower side Green 139C–139D |
| Color mature stage | Upper side Green 137A–138A Lower side Green 138A–138B |
| Color midvein mature leaf | Upper side Yellow-green 147D Under side Yellow-green 145D |
| Size | Medium; length 11 cm, width 7 cm |
| Quantity (number per single stem) | 28 |
| Shape | Cordiform |
| Texture upper side | Fleshy and glabrous |
| Texture under side | Pubescent |
| Venation arrangement | Palmate |
| Shape of the margin | Lobed - serrated |
| Shape of Base of Sinus Between Lateral Lobes | Rounded |
| Margin of Sinus Between Lateral Lobes | Converging |
| Shape of Base | Truncate |
| Apex | Mucronulate |
| Petiole Length | 2 cm |
| Petiole Color | Yellow-green 147D |

TABLE 2

| Differences with the comparison Varieties | | | |
|---|---|---|---|
| | 'Artist Orange' | 'Artist Yellow' | 'Orange Reagan' |
| Color upper side ray-florets | Orange 29A and Red 45B | Yellow-orange 14B and Red 46A | Greyed-orange 169A–169B |
| Color lower side ray-florets | Greyed-orange 164C and greyed-orange 173B | Yellow-orange 14C and Red 46B | Greyed-orange 163B |

I claim:

1. A new and distinct variety of *chrysanthemum* plant as described and illustrated.

* * * * *